United States Patent
Chereze et al.

(10) Patent No.: US 7,547,705 B2
(45) Date of Patent: Jun. 16, 2009

(54) **SUBSTITUTED 8'-PYRI(MI)DINYL-DIHYDROSPIRO-[CYCLOALKYLAMINE]-PYRIMIDO[1,2-*A*] PYRIMIDIN-6-ONE DERIVATIVES**

(75) Inventors: Nathalie Chereze, Bourg la Reine (FR); Alistair Lochead, Charenton le Pont (FR); Mourad Saady, Paris (FR); Franck Slowinski, Thieux (FR); Philippe Yaiche, Les Lilas (FR)

(73) Assignees: Sanofi-Aventis, Paris (FR); Mitsubishi Pharma Corporation, Osaka (JP)

( * ) Notice: Subject to any disclaimer, the term of this patent is extended or adjusted under 35 U.S.C. 154(b) by 0 days.

(21) Appl. No.: 11/866,687

(22) Filed: Oct. 3, 2007

(65) Prior Publication Data
US 2008/0081820 A1 Apr. 3, 2008

Related U.S. Application Data

(60) Division of application No. 11/423,557, filed on Jun. 12, 2006, now Pat. No. 7,294,631, which is a continuation of application No. PCT/EP2004/014846, filed on Dec. 17, 2004.

(30) Foreign Application Priority Data

Dec. 19, 2003 (EP) .................................. 03293236

(51) Int. Cl.
*A61K 31/397* (2006.01)
*A61K 31/551* (2006.01)
*A61K 31/527* (2006.01)
*A61K 31/4162* (2006.01)
*C07D 225/00* (2006.01)
*C07D 223/00* (2006.01)
*C07D 487/20* (2006.01)
*C07D 239/00* (2006.01)
*A61P 3/10* (2006.01)
*A61P 25/28* (2006.01)
*A61P 25/16* (2006.01)
*A61P 25/18* (2006.01)

(52) U.S. Cl. ............. 514/267; 514/210.16; 514/212.02; 514/220; 540/466; 540/543

(58) Field of Classification Search ............. 514/259.1, 514/267, 210.06, 212.02, 220, 387
See application file for complete search history.

(56) References Cited

U.S. PATENT DOCUMENTS
2005/0267132 A1 12/2005 Banville et al.

FOREIGN PATENT DOCUMENTS
WO WO 02/18386 3/2002
WO WO 03/027115 4/2003
WO WO 03/027116 4/2003

OTHER PUBLICATIONS

Bhat, et al., J. Neurochem., 2004, 89, 1313-1317.*
Martinez, et al., Med. Res. Rev., vol. 22, No. 4, 373-384 (2002).*
Buée, et al., Brain Res. Rev., 33 (2000) 95-130.*
Henriksen, et al., Curr. Drug Targets, 2006, 7 (11), 1435-42 (Abstract).*
Gould et al., Curr. Drug Targets, Nov. 7, 2006(11): 1399-409 (Abstract).*
Harwood, Curr. Mol. Med., Aug. 2003; 3(5): 472-82 (abstract).*
Zhao, et al., Schizophr. Res., May 2006; 84(1). Epub Apr. 11, 2006 (Abstract).*
Gould, Expert Opin. Ther. Targets, Jun. 2006; 10(3):377-92 (Abstract).*
Kwok, et al., Annals of Neurology, vol. 58, No. 6, Dec. 2005, pp. 829-839.*
Nadri, et al., Schizophrenia Research, 71 (2004), 377-382.*
Vippagunta et al. Advanced Drug Delivery Reviews, 2001, 48, 3-26.*
Griesser, Chapter 8, The Importance of Solvates (pp. 211-230), in the text, Polymorphism: In the Pharmaceutical Industry, Hilfiker, 2006.*
Brittain, Chapter V of Polymorphism in Pharmaceutical Solids, 1999, pp. 126-127.*

* cited by examiner

*Primary Examiner*—Mark L Berch
*Assistant Examiner*—Cecilia M Jaisle
(74) *Attorney, Agent, or Firm*—Balaram Gupta

(57) ABSTRACT

The invention relates to a dihydrospiro-[cycloalkylamine]-pyrimidone derivative represented by formula (I) or a salt thereof:

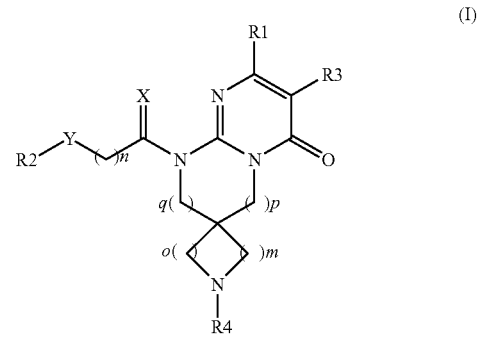

wherein: X, Y, R1, R2, R3, R4, o, m, n, p and q are as defined herein. The invention relates also to a medicament comprising the said derivative or a salt thereof as an active ingredient which is used for preventive and/or therapeutic treatment of a neurodegenerative disease caused by abnormal activity of GSK3β, such as Alzheimer disease.

5 Claims, No Drawings

SUBSTITUTED 8'-PYRI(MI)DINYL-DIHYDROSPIRO-[CYCLOALKYLAMINE]-PYRIMIDO[1,2-A] PYRIMIDIN-6-ONE DERIVATIVES

CROSS REFERENCE TO RELATED APPLICATIONS

This application is a division of U.S. application Ser. No. 11/423,557, filed Jun. 12, 2006, now allowed, which is a continuation of International application No. PCT/EP 2004/014,846, filed Dec. 17, 2004, which is incorporated herein by reference in its entirety; which claims the benefit of priority of European Patent Application No. 03293236.0, filed Dec. 19, 2003.

TECHNICAL FIELD

The present invention relates to compounds that are useful as an active ingredient of a medicament for preventive and/or therapeutic treatment of neurodegenerative diseases caused by abnormal activity of GSK3β.

BACKGROUND ART

GSK3β (glycogen synthase kinase 3β) is a proline directed serine, threonine kinase that plays an important role in the control of metabolism, differentiation and survival. It was initially identified as an enzyme able to phosphorylate and hence inhibit glycogen synthase. It was later recognized that GSK3β was identical to tau protein kinase 1 (TPK1), an enzyme that phosphorylates tau protein in epitopes that are also found to be hyperphosphorylated in Alzheimer's disease and in several taupathies. Interestingly, protein kinase B (AKT) phosphorylation of GSK3β results in a loss of its kinase activity, and it has been hypothesized that this inhibition may mediate some of the effects of neurotrophic factors. Moreover, phosphorylation by GSK3β of β-catenin, a protein involved in cell survival, results in its degradation by an ubiquitinilation dependent proteasome pathway.Thus, it appears that inhibition of GSK3β activity may result in neurotrophic activity. Indeed there is evidence that lithium, an uncompetitive inhibitor of GSK3β, enhances neuritogenesis in some models and also increases neuronal survival, through the induction of survival factors such as Bcl-2 and the inhibition of the expression of proapoptotic factors such as P53 and Bax.

Recent studies have demonstrated that β-amyloid increases the GSK3β activity and tau protein phosphorylation. Moreover, this hyperphosphorylation as well as the neurotoxic effects of β-amyloid are blocked by lithium chloride and by a GSK3β antisense mRNA. These observations strongly suggest that GSK3β may be the link between the two major pathological processes in Alzheimer's disease: abnormal APP (Amyloid Precursor Protein) processing and tau protein hyperphosphorylation.

Although tau hyperphosphorylation results in a destabilization of the neuronal cytoskeleton, the pathological consequences of abnormal GSK3β activity are,most likely, not only due to a pathological phosphorylation of tau protein because, as mentioned above, an excessive activity of this kinase may affect survival through the modulation of the expression of apoptotic and antiapoptotic factors.Moreover, it has been shown that β-amyloid-induced increase in GSK3β activity results in the phosphorylation and, hence the inhibition of pyruvate dehydrogenase, a pivotal enzyme in energy production and acetylcholine synthesis.

Altogether these experimental observations indicate that GSK3β may find application in the treatment of the neuropathological consequences and the cognitive and attention deficits associated with Alzheimer's disease, as well as other acute and chronic neurodegenerative diseases. These include, in a non-limiting manner, Parkinson's disease, tauopathies (e.g. frontotemporoparietal dementia, corticobasal degeneration, Pick's disease, progressive supranuclear palsy) and other dementia including vascular dementia; acute stroke and others traumatic injuries; cerebrovascular accidents (e.g. age related macular degeneration); brain and spinal cord trauma; peripheral neuropathies; retinopathies and glaucoma.

In addition GSK3β may find application in the treatment of other diseases such as:Non-insulin dependent diabetes (such as diabetes type II) and obesity; manic depressive illness; schizophrenia; alopecia; cancers such as breast cancer, non-small cell lung carcinoma, thyroid cancer, T or B-cell leukemia and several virus-induced tumors.

DISCLOSURE OF THE INVENTION

An object of the present invention is to provide compounds useful as an active ingredient of a medicament for preventive and/or therapeutic treatment of a disease caused by abnormal GSK3β activity, more particularly of neurodegenerative diseases. More specifically, the object is to provide novel compounds useful as an active ingredient of a medicament that enables prevention and/or treatment of neurodegenerative diseases such as Alzheimer's disease.

Thus, the inventors of the present invention have identified compounds possessing inhibitory activity against GSK3β. As a result, they found that compounds represented by the following formula (I) had the desired activity and were useful as an active ingredient of a medicament for preventive and/or therapeutic treatment of the aforementioned diseases.

The present invention thus provides dihydrospiro-[cycloalkylamine]-pyrimidone (or pyrimidione) derivatives represented by formula (I) or salts thereof, solvates thereof or hydrates thereof:

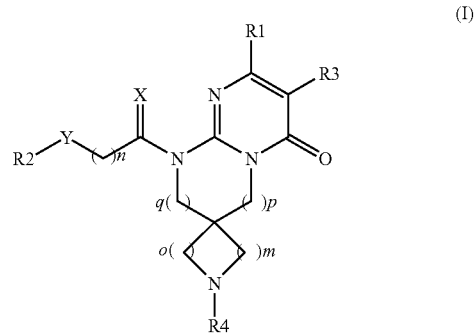

wherein:

X represents two hydrogen atoms, a sulfur atom, an oxygen atom or a $C_{1-2}$ alkyl group and a hydrogen atom;

Y represents a bond, a carbonyl group, a methylene group optionally substituted by one or two groups chosen from a $C_{1-6}$ alkyl group, a hydroxyl group, a $C_{1-4}$ alkoxy group, a $C_{1-2}$ perhalogenated alkyl group or an amino group;

R1 represents a 2, 3 or 4-pyridine ring or a 2, 4 or 5-pyrimidine ring, the ring being optionally substituted by a $C_{1-4}$ alkyl group, a $C_{1-4}$ alkoxy group, or a halogen atom;

R2 represents a benzene ring or a naphthalene ring; the rings being optionally substituted by 1 to 4 substituents selected from a $C_{1-6}$ alkyl group, a methylendioxy group, a halogen atom, a $C_{1-2}$ perhalogenated alkyl group, a $C_{1-3}$ halogenated alkyl group, a hydroxyl group, a $C_{1-4}$ alkoxy group, a nitro, a cyano, an amino, a $C_{1-5}$ monoalkylamino group or a $C_{2-10}$ dialkylamino group;

R3 represents a hydrogen atom, a $C_{1-6}$ alkyl group or a halogen atom;

R4 represents a hydrogen atom, a $C_{1-4}$ alkoxy carbonyl group, a $C_{3-6}$ cycloalkyl carbonyl group, a benzoyl group, a $C_{1-6}$ alkyl group, the groups being optionally substituted by 1 to 4 substituents selected from a halogen atom, a hydroxyl group or a $C_{1-4}$ alkoxy group;

o and m represent 1 to 2;
n represents 0 to 3;
p represents 0 to 2; and
q represents 0 to 2.

Dihydrospiro-[cycloalkylamine]-pyrimidone derivates represented by formula (I) or salts thereof, solvates thereof or hydrates, wherein X, Y, R1, R2, R3, O, n, p, q, are as defined hereinabove and R4 represents a hydrogen atom, a $C_{1-4}$alkoyl carbonyl group, $C_{1-6}$ alkyl group optionally substituted by 1 to 4substituents selected frona halogen atom, a hydroxyl group or a $C_{1-4}$ alkoxy group; represent another object of the invention.

According to another aspect of the present invention, there is provided a medicament comprising as an active ingredient a substance selected from the group consisting of the pyrimidone derivatives represented by formula (I) and the physiologically acceptable salts thereof, and the solvates thereof and the hydrates thereof. As preferred embodiments of the medicament, there are provided the aforementioned medicament which is used for preventive and/or therapeutic treatment of diseases caused by abnormal GSK3β activity, and the aforementioned medicament which is used for preventive and/or therapeutic treatment of neurodegenerative diseases and in addition other diseases such as: Non-insulin dependent diabetes (such as diabetes type II) and obesity; manic depressive illness; schizophrenia; alopecia; cancers such as breast cancer, non-small cell lung carcinoma, thyroid cancer, T or B-cell leukemia and several virus-induced tumors.

As further preferred embodiments of the present invention, there are provided the aforementioned medicament wherein the diseases are neurodegenerative diseases and are selected from the group consisting of Alzheimer's disease, Parkinson's disease, tauopathies (e.g. frontotemporoparietal dementia, corticobasal degeneration, Pick's disease, progressive supranuclear palsy) and other dementia including vascular dementia; acute stroke and others traumatic injuries; cerebrovascular accidents (e.g. age related macular degeneration); brain and spinal cord trauma; peripheral neuropathies; retinopathies and glaucoma, and the aforementioned medicament in the form of pharmaceutical composition containing the above substance as an active ingredient together with one or more pharmaceutical additives.

The present invention further provides an inhibitor of GSK3β activity comprising as an active ingredient a substance selected from the group consisting of the dihydrospiro-[cycloalkylamine]-pyrimidone derivatives of formula (I) and the salts thereof, and the solvates thereof and the hydrates thereof.

According to further aspects of the present invention, there is provided a method for preventive and/or therapeutic treatment of neurodegenerative diseases caused by abnormal GSK3β activity, which comprises the step of administering to a patient a preventively and/or therapeutically effective amount of a substance selected from the group consisting of dihydrospiro-[cycloalkylamine]-pyrimidone derivatives of formula (I) and the physiologically acceptable salts thereof, and the solvates thereof and the hydrates thereof; and a use of a substance selected from the group consisting of the dihydrospiro-[cycloalkylamine]-pyrimidone derivatives of formula (I) and the physiologically acceptable salts thereof, and the solvates thereof and the hydrates thereof for the manufacture of the aforementioned medicament.

As used herein, the $C_{1-6}$ alkyl group represents a straight or branched alkyl group having 1 to 6 carbon atoms, for example, methyl group, ethyl group, n-propyl group, isopropyl group, n-butyl group, isobutyl group, sec-butyl group, tert-butyl group, n-pentyl group, isopentyl group, neopentyl group, 1,1-dimethylpropyl group, n-hexyl group, isohexyl group, and the like;

The $C_{3-6}$ cycloalkyl group represents a cyclic alkykl group having 3 to 6 carbon atoms, for example, cyclopropyl group, cyclobutyl group, cyclopentyl group, cyclohexyl group, and then like;

The $C_{1-4}$ alkoxy group represents an alkyloxy group having 1 to 4 carbon atoms for example, methoxy group, ethoxy group, propoxy group, isopropoxy group, butoxy group, isobutoxy group, sec-butoxy group, tert-butoxy group, and the like;

The halogen atom represents a fluorine, chlorine, bromine or iodine atom;

The $C_{1-2}$ perhalogenated alkyl group represents an alkyl group wherein all the hydrogen have been substituted by a halogeno, for example a $CF_3$ or $C_2F_5$;

The $C_{1-3}$ halogenated alkyl group represents an alkyl group wherein at least one hydrogen has not been substituted by an halogen atom;

The $C_{1-5}$ monoalkylamino group represents an amino group substituted by one $C_{1-6}$ alkyl group, for example, methylamino group, ethylamino group, propylamino group, isopropylamino group, butylamino group, isobutylamino group, tert-butylamino group, pentylamino group and isopentylamino group;

The $C_{2-10}$ dialkylamino group represents an amino group substituted by two $C_{1-5}$ alkyl groups, for example, dimethylamino group, ethylmethylamino group, diethylamino group, methylpropylamino group and diisopropylamino group;

A leaving group L represents a group which could be easily cleaved and substituted, such a group may be for example a tosyl, a mesyl, a bromide and the like.

The compounds represented by the aforementioned formula (I) may form a salt, Examples of the salt include, when an acidic group exists, salts of alkali metals and alkaline earth metals such as lithium, sodium, potassium, magnesium, and calcium; salts of ammonia and amines such as methylamine, dimethylamine, trimethylamine, dicyclohexylamine, tris(hydroxymethyl)aminomethane, N,N-bis (hydroxyethyl)piperazine, 2-amino-2-methyl-1-propanol, ethanolamine, N-methylglucamine, and L-glucamine; or salts with basic amino acids such as lysine, δ-hydroxylysine, and arginine. The base-addition salts of acidic compounds are prepared by standard procedures well known in the art.

When a basic group exists, examples include salts with mineral acids such as hydrochloric acid, hydrobromic acid, sulfuric acid, nitric acid, phosphoric acid;salts with organic acids such as methanesulfonic acid, benzenesulfonic acid, p-toluenesulfonic acid, acetic acid, propionic acid, tartaric acid, fumaric acid, maleic acid, malic acid, oxalic acid, succinic acid, citric acid, benzoic acid, mandelic acid, cinnamic acid, lactic acid, glycolic acid, glucuronic acid, ascorbic acid, nicotinic acid, and salicylic acid; or salts with acidic amino acids such as aspartic acid, and glutamic acid.

The acid-addition salts of the basic compounds are prepared by standard procedures well know in the art which include, but are not limited thereto, dissolving the free base in an aqueous alcohol solution containing the appropriate acid and isolating the salt by evaporating the solution, or by reacting the free base and an acid in an organic solvent, in which case the salt separates directly, or is precipitated with a second organic solvent, or can be obtained by concentration of the solution. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial properties inherent in the free base are not compromised by side effects ascribable to the anions. Although medicinally acceptable salts of the basic compounds are preferred, all acid-addition salts are within the scope of the present invention.

In addition to the dihydrospiro-[cycloalkylamine]-pyrimidone derivatives represented by the aforementioned formula (I) and salts thereof, their solvates and hydrates also fall within the scope of the present invention.

The dihydrospiro-[cycloalkylamine]-pyrimidone derivatives represented by the aforementioned formula (I) may have one or more asymmetric carbon atoms. As for the stereochemistry of such asymmetric carbon atoms, they may independently be in either (R) and (S) configuration, and the derivative may exist as stereoisomers such as optical isomers, or diastereoisomers. Any stereoisomers in pure form, any mixtures of stereoisomers, racemates and the like fall within the scope of the present invention.

Examples of preferred compounds of the present invention are shown in table 1 hereinafter. However, the scope of the present invention is not limited by these compounds.

Preferred compounds of the present invention represented by formula (I) include also compounds wherein:
(1) R1 represents a 3- or 4-pyridine ring and more preferably 4-pyridine ring or a 4- or 5-pyrimidine ring and more preferably 4-pyrimidine ring, which may be substituted by a $C_{1-2}$ alkyl group, a $C_{1-2}$ alkoxy group or a halogen atom; and/or
(2) R2 represents a benzene ring or a naphthalene ring, the ring being optionally substituted 1 to 4 substituents selected from a $C_{1-3}$ alkyl group, a halogen atom, a hydroxyl group or a $C_{1-2}$ alkoxy group; and/or
(3) R3 represents a hydrogen atom, a $C_{1-3}$ alkyl group or a halogen atom; more preferably a hydrogen atom; and/or
(4) R4 represents a hydrogen atom, a $C_{1-4}$ alkoxy carbonyl group, a $C_{1-3}$ cycloalkyl carbonyl group, a benzoyl group, a $C_{1-3}$ alkyl group,; the groups being optionally substituted by 1 to 4 substituents selected from a halogen atom, a hydroxyl group or a $C_{1-4}$ alkoxy group; and/or
(5) Y represents a carbonyl group or methylene group optionally substituted by one or two groups chosen from a $C_{1-3}$ alkyl group, a hydroxyl group, a $C_{1-4}$ alkoxy group, a $C_{1-2}$ perhalogenated alkyl group, an amino group; and more particularly wherein R1, R2, R3, R4 and Y are as defined hereinabove.

More preferred compounds of the present invention represented by formula (I) include also compounds wherein:
(1) R1 represents an unsubstituted 4-pyridine ring or 4-pyrimidine ring; and/or
(2) R2 represents a benzene ring, the ring being optionally substituted 1 to 4 substituents selected from a $C_{1-3}$ alkyl group, a halogen atom, a hydroxyl group or a $C_{1-2}$ alkoxy group; and/or
(3) R3 represents a hydrogen atom; and/or
(4) R4 represents a $C_{1-4}$ alkoxy carbonyl group, a $C_{3-6}$ cycloalkyl group, a benzoyl group or a $C_{1-3}$ alkyl group optionally substituted by 1 to 4 substituents selected from a halogen atom or a hydroxyl group; and/or
(5) X represents two hydrogen atoms; and/or
(6) Y represents a carbonyl group or a methylene group optionally substituted by a hydroxyl group; and/or
(7) p represents 2 and q represents 0; and more particularly wherein R1, R2, R3, X, Y, p, q, m, o and n are as defined hereinabove.

Particularly preferred compounds of the present invention represented by formula (I), wherein R1 is a pyridine ring or a pyrimidine ring, include compounds of table 1, whose names are as set forth below:

1. Ethyl-1'-[(2S)-2-hydroxy-2-phenylethyl]-6'-oxo-8'-(pyridin-4-yl)-1',3',4',6'-tetrahydro-1H-spiro[piperidine-4,2'-pyrimido[1,2-a]pyrimidine]-1-carboxylate
2. Ethyl-6'-oxo-1'-[2-oxo-2-phenylethyl]-8'-(pyridin-4-yl)-1',3',4',6'-tetrahydro-1H-spiro[piperidine-4,2'-pyrimido[1,2-a]pyrimidine]-1-carboxylate
3. 1'-[(2S)-2-Hydroxy-2-phenylethyl]-1-methyl-8'-(pyridin-4-yl)-3',4'-dihydrospiro[piperidine-4,2'-pyrimido[1,2-a]pyrimidin]-6'(1'H)-one
4. 1-Methyl-1'-(2-oxo-2-phenylethyl)-8'-(pyridin-4-yl)-3',4'-dihydrospiro[piperidine-4,2'-pyrimido[1,2-a]pyrimidin]-6'(1'H)-one
5. Ethyl-1'-[(2S)-2-hydroxy-2-phenylethyl]-6'-oxo-8'-(pyrimidin-4-yl)-1',3',4',6'-tetrahydro-1H-spiro[piperidine-4,2'-pyrimido[1,2-a]pyrimidine]-1-carboxylate
6. Ethyl-6'-oxo-1'-[2-oxo-2-phenylethyl]-8'-(pyrimidin-4-yl)-1',3',4',6'-tetrahydro-1H-spiro[piperidine-4,2'-pyrimido[1,2-a]pyrimidine]-1-carboxylate
7. 1'-[(2S)-2-Hydroxy-2-phenylethyl]-1-methyl-8'-(pyrimidin-4-yl)-3',4'-dihydrospiro[piperidine-4,2'-pyrimido[1,2-a]pyrimidin]-6'(1'H)-one;
8. 1-(Cyclohexylcarbonyl)-1'-[(2S)-2-hydroxy-2-phenylethyl]-8'-pyridin-4-yl-3',4'-dihydrospiro[piperidine-4,2'-pyrimido[1,2-a]pyrimidin]-6'(1'H)-one
9. 1-(Cyclohexylcarbonyl)-1'-(2-oxo-2phenylethyl)-8'-pyridin-4yl-3',4'-dihydrospiro [piperidine-4,2'-pyrimido[1,2-a]pyrimidin]-6'(1'H)-one
10. 1-(3-Fluorobenzoyl)-1'-[(2S)-2-hydroxy-2-phenylethyl]-8'-pyridin-4-yl-3',4'-dihydrospiro[piperidine-4,2'-pyrimido[1,2-a]pyrimidin]-6'(1'H)-one
11. 1(3-Fluorobenzoyl)-1'-(2-oxo-2phenylethyl)-8'-pyridin-4yl-3',4'-dihydrospiro [piperidine-4,2'-pyrimido[1,2-a]pyrimidin]-6'(1'H)-one
12. 1-(Cyclobutylcarbonyl)-1'-[(2S)-2-hydroxy-2-phenylethyl]-8'-pyridin-4-yl-3',4'-dihydrospiro[piperidine-4,2'-pyrimido[1,2-a]pyrimidin]-6'(1'H)-one
13. 1-(Cyclobutylcarbonyl)-1'-(2-oxo-2phenylethyl)-8'-pyridin-4yl-3',4'-dihydrospiro [piperidine-4,2'-pyrimido[1,2-a]pyrimidin]-6'(1'H)-one
14. 1-(Cyclobutylcarbonyl))-1'-[(2S)-2-hydroxy-2-phenylethyl]-8'-pyridin-4-yl-3',4'-dihydrospiro[piperidine-4,2'-pyrimido[1,2-a]pyrimidin]-6'(1'H)-one
15. 1-(Cyclobutylcarbonyl)-1'-(2-oxo-2phenylethyl)-8'-pyridin-4yl-3',4'-dihydrospiro [piperidine-4,2'-pyrimido[1,2-a]pyrimidin]-6'(1'H)-one
16. 1-Methyl-1'-(2-oxo-2-phenylethyl)-8-(pyrimidin-4-yl)-3',4'-dihydrospiro [piperidine-4,2'-pyrimido[1,2-a]pyrimidin]-6'(1'H)-one and compounds of table 2, include the following:
1. Ethyl 1-[(2S)-2-hydroxy-2-phenylethyl]6-oxo-8-(pyridin-4-yl)-1,3,4,6-tetrahydro-1'H-spiro[pyrimido[1,2-a]pyrimidine-2,3'-pyrrolidine]-1'-carboxylate
2. Ethyl 6-oxo-1-(2-oxo-2-phenylethyl)-8-(pyridin-4-yl)-1,3,4,6-tetrahydro-1'H-spiro [pyrimido[1,2-a]pyrimidine-2,3'-pyrrolidine]-1'-carboxylate
3. 1-[(2S)-2-hydroxy-2-phenylethyl]-1'-methyl-8-(pyridin-4-yl)-3,4-dihydrospiro [pyrimido[1,2-a]pyrimidine-2,3'-pyrrolidin]-6(1H)-one
4. 1'-Methyl-1-(2-oxo-2-phenylethyl)-8-(pyridin-4-yl)-3,4-dihydrospiro (pyrimido[1,2-a]pyrimidine-2,3'-pyrrolidin]-6(1H)-one.
5. Ethyl 1-[(2S)-2-hydroxy-2-phenylethyl]-6-oxo-8pyrimidin-4yl-1,3,4,6-tetrahydro-1'H-spiro[pyrimido[1,2-a]pyrimidine-2,3'-pyrrolidine]-1'-carboxylate
6. Ethyl6-oxo-1-(2-oxo-2-phenylethyl)-8-pyrimidin-4-yl-1,3,4,6-etrahydro-1'H-spiro [pyrimido[1,2-a]pyrimidine-2,3'-pyrrolidine]-1'-carboxylate
7. 1'-(3-Fluorobenzoyl)-1-[(2S)-2-hydroxy-2-phenylethyl]-8-pyrimidin-4-yl-3,4-dihydrospiro [pyrimido[1,2-a]pyrimidine-2,3'-pyrrolidin]-6(1H)-one
8. 1'-(3-Fluorobenzoyl)-1-(2-oxo-2-phenylethyl)-8-pyrimidin-4-yl-3,4-dihydrospiro [pyrimido[1,2-a]pyrimidine-2,3'-pyrrolidin]-6(1H)-one
9. 1'-(3-Fluorobenzoyl) -1-[(2S)-2-hydroxy-2-phenylethyl]-8-pyridin-4-yl-3,4-dihydrospiro [pyrimido[1,2-a]pyrimidine-2,3'-pyrrolidin]-6(1H)-one
10. 1'-(3-Fluorobenzoyl)-1-(2-oxo-2-phenylethyl)-8-pyridin-4-yl-3,4-dihydrospiro [pyrimido[1,2-a]pyrimidine-2,3'-pyrrolidin]-6(1H)-one
11. 1'(Cyclopropylcarbonyl)-1-[(2S)-2-hydroxy-2-phenylethyl]-8-pyridin-4-yl-3,4-dihydrospiro [pyrimido[1,2-a]pyrimidine-2,3'-pyrrolidin]-6(1H)-one
12. 1'(Cyclopropylcarbonyl)-1-(2-oxo-2-phenylethyl)-8-pyridin-4-yl-3,4-dihydrospiro [pyrimido[1,2-a]pyrimidine-2,3'-pyrrolidin]-6(1H)-one
13. 1'(Cyclopropylcarbonyl)-1-[(2S)-2-hydroxy-2-phenylethyl]-8-pyrimidin-4-yl-3,4-dihydrospiro [pyrimido[1,2-a]pyrimidine-2,3'-pyrrolidin]-6(1H)-one
14. 1'(Cyclopropylcarbonyl)-1-(2-oxo-2-phenylethyl)-8-pyrimidin-4-yl-3,4-dihydrospiro [pyrimido[1,2-a]pyrimidine-2,3'-pyrrolidin]-6(1H)-one
15. 1'(Cyclobutylcarbonyl)-1-[(2S)-2-hydroxy-2-phenylethyl]-8-pyrimidin-4-yl-3,4-dihydrospiro [pyrimido[1,2-a]pyrimidine-2,3'-pyrrolidin]-6(1H)-one
16. 1'(Cyclobutylcarbonyl)-1-(2-oxo-2-phenylethyl)-8-pyrimidin-4-yl-3,4-dihydrospiro [pyrimido[1,2-a]pyrimidine-2,3'-pyrrolidin]-6(1H)-one
17. 1'(Cyclobutylcarbonyl)-1-[(2S)-2-hydroxy-2-phenylethyl]-8-pyridin-4-yl-3,4-dihydrospiro [pyrimido[1,2-a]pyrimidine-2,3'-pyrrolidin]-6(1H)-one
18. 1'(Cyclobutylcarbonyl)-1-(2-oxo-2-phenylethyl)-8-pyridin-4-yl-3,4-dihydrospiro [pyrimido[1,2-a]pyrimidine-2,3'-pyrrolidin]-6(1H)-one
19. 1'(Cyclohexylcarbonyl)-1-[(2S)-2-hydroxy-2-phenylethyl]-8-pyridin-4-yl-3,4-dihydrospiro [pyrimido[1,2-a]pyrimidine-2,3'-pyrrolidin]-6(1H)-one
20. 1'(Cyclohexylcarbonyl)-1-(2-oxo-2-phenylethyl)-8-pyridin-4-yl-3,4-dihydrospiro [pyrimido[1,2-a]pyrimidine-2,3'-pyrrolidin]-6(1H)-one
21. 1'(Cyclohexylcarbonyl)-1-[(2S)-2-hydroxy-2-phenylethyl]-8-pyrimidin-4-yl-3,4-dihydrospiro [pyrimido[1,2-a]pyrimidine-2,3'-pyrrolidin]-6(1H)-one
22. 1'(Cyclohexylcarbonyl) -1-(2-oxo-2-phenylethyl)-8-pyrimidin-4-yl-3,4-dihydrospiro [pyrimido[1,2-a]pyrimidine-2,3'-pyrrolidin]-6(1H)-one As a further object, the present invention concerns also methods for preparing the dihydrospiro-[cycloalkylamine]-pyrimidone compounds represented by the aforementioned formula (I).

These compounds can be prepared, for example, according to methods explained below.

Preparation Method

Dihydrospiro-[cycloalkylamine]-pyrimidone compounds represented by the aforementioned formula (I), may be prepared according to the method described in the scheme 1.

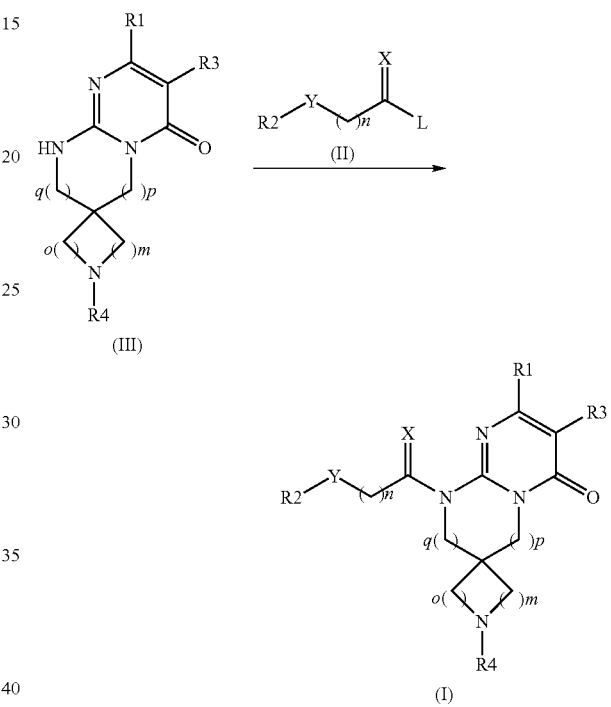

Scheme 1

(In the above scheme the definition of R1, R2, R3, R4, X, Y, m, n, o, p and q are the same as those already described for compound of formula (I)).

Following this method, the pyrimidinone derivative represented by the above formula (III), wherein R1, R3, R4, m, n, o, p and q are as defined for compound of formula (I), is allowed to react with a base such as sodium hydride, sodium carbonate or potassium carbonate in a solvent such as N,N-dimethylformamide, N-methylpyrrolidone, N,N-dimethylacetamide or chloroform at a suitable temperature ranging from 0 to 130° C. under ordinary air, then with a compound of formula (II), wherein R2, X, Y and n are as defined for compound of formula (I) and L represents a leaving group preferably bromide or mesyl group, to obtain the compound of the aforementioned formula (I).

Alternatively compounds of formula (I) wherein Y represents a carbonyl group may be prepared by oxydation of a compound of formula (I) wherein Y represents a methylene group substituted by a hydroxyl group according to methods well known to one skilled in the art.

Compound of formula (II) is commercially available or may be synthesized according to well-known methods to one skilled in the art.

Compound of formula (III) may be prepared according to the method defined in scheme 2.

Scheme 2.

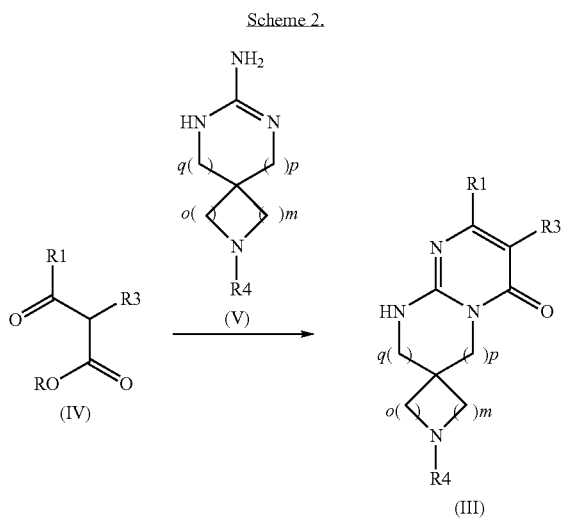

(In the above scheme the definition of R1, R3, R4, m, o, p and q are the same as already described.)

According to this method, the 3-ketoester of formula (IV), wherein R1 and R3 are as defined for compound of formula (I) and R is an alkyl group such as for example methyl or ethyl, is allowed to react with a compound of formula (V). The reaction may be carried out in the presence of a base such as potassium carbonate, in an alcoholic solvent such as methanol, ethanol and the like or without, at a suitable temperature ranging from 25° to 140° C. under ordinary air.

Alternatively, compound of formula (III) wherein R3 represents a hydrogen atom may be halogenated in order to give compounds of formula (III) wherein R3 is a halogen atom such as a bromine atom or a chlorine atom. The reaction may be carried out in an acidic medium such as acetic acid or propionic acid, in presence of bromosuccinimide or chlorosuccinimide, or bromine.

In addition, compounds of formula (III) wherein R3 represents a fluorine atom may be obtained by analogy to the method described in Tetrahedron Letters, Vol. 30, N°45, pp 6113-6116, 1989 incorporated herein by reference in its entirety.

Compound of formula (IV) is commercially available or may be synthesized according to well-known methods to one skilled in the art.

For example compounds of formula (IV), wherein R1 represent a pyridine ring or a pyrimidine ring, optionally substituted by a $C_{1-4}$ alkyl group, $C_{1-4}$ alkoxy group or a halogen atom, can be prepared by reacting respectively an isonicotinic acid or a pyrimidine-carboxylic acid, optionally substituted by a $C_{1-4}$ alkyl group, $C_{1-4}$ alkoxy group or a halogen, with the corresponding malonic acid monoester. The reaction can be carried out using methods well known to one skilled in the art, such as for example in presence of a coupling agent such as 1,1'-carbonylbis-1H-imidazole in a solvent such as tetrahydrofuran at a temperature ranging from 20 to 70° C.

Compound of formula (V) may be synthesized according to well-known methods of one skilled in the art.

For example compound of formula (V), when m and o represent 2, p represents 2 and q represents 0, may be prepared according to the method defined in scheme 3 and starting from compound (VI), wherein R4 is as defined for formula (I) The conditions which may be used are given in the chemical examples.

Scheme 3

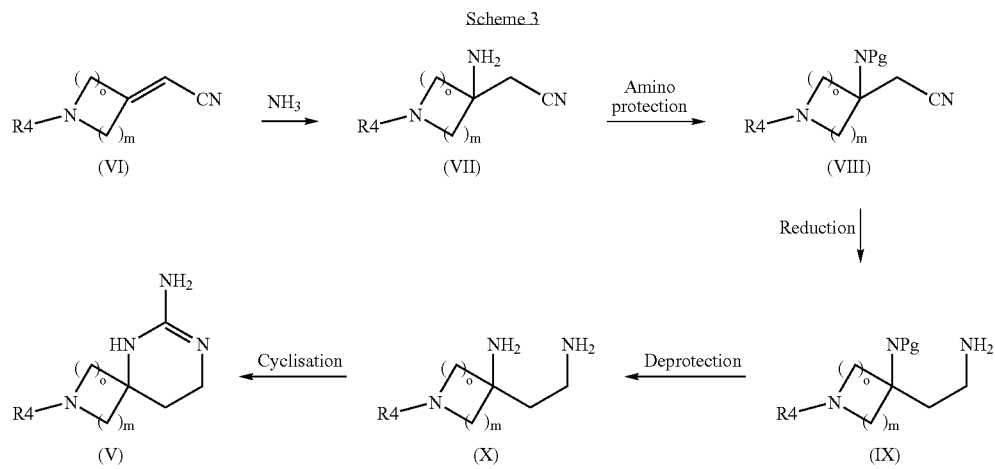

(In the above scheme Pg represents an amino-protecting group and L a leaving group)

Compound of formula (VI) may be synthesized according to the method described in *J. Med. Chem.* 1991, 34, 90-97, which is incorporated herein by reference in its entirety.

Compound of formula (VII) may be synthesized according to the method described in *Synthetic Communication* 28(4), 701-712 (1998),which is incorporated herein by referencein in its entirety.

As a further object, the present invention concerns also the compounds of formula (III) as intermediates of compounds of formula (I).

In the above reactions protection or deprotection of a functional group may sometimes be necessary. A suitable protecting group Pg can be chosen depending on the type of the functional group, and a method described in the literature may be applied. Examples of protecting group, of protection and deprotection methods are given for example in Protective groups in Organic Synthesis Greene et al., 2nd Ed. (John Wiley & Sons, Inc., New York).

The compounds of the present invention have inhibitory activity against GSK3β. Accordingly, the compounds of the present invention are useful as an active ingredient for the preparation of a medicament, which enables preventive and/or therapeutic treatment of a disease caused by abnormal GSK3β activity and more particularly of neurodegenerative diseases such as Alzheimer's disease. In addition, the compounds of the present invention are also useful as an active ingredient for the preparation of a medicament for preventive and/or therapeutic treatment of neurodegenerative diseases such as Parkinson's disease, tauopathies (e.g. frontotemporoparietal dementia, corticobasal degeneration, Pick's disease, progressive supranuclear palsy) and other dementia including vascular dementia; acute stroke and others traumatic injuries; cerebrovascular accidents (e.g. age related macular degeneration); brain and spinal cord trauma; peripheral neuropathies; retinopathies and glaucoma; and other diseases such as non-insulin dependent diabetes (such as diabetes type II) and obesity; manic depressive illness; schizophrenia; alopecia; cancers such as breast cancer, non-small cell lung carcinoma, thyroid cancer, T or B-cell leukemia and several virus-induced tumors.

The present invention further relates to a method for treating neurodegenerative diseases caused by abnormal activity of GSK3β and of the aforementioned diseases which comprises administering to a mammalian organism in need thereof an effective amount of a compound of the formula (I).

As the active ingredient of the medicament of the present invention, a substance may be used which is selected from the group consisting of the compound represented by the aforementioned formula (I) and pharmacologically acceptable salts thereof, and solvates thereof and hydrates thereof. The substance, per se, may be administered as the medicament of the present invention, however, it is desirable to administer the medicament in a form of a pharmaceutical composition which comprises the aforementioned substance as an active ingredient and one or more pharmaceutical additives. As the active ingredient of the medicament of the present invention, two or more of the aforementioned substances may be used in combination. The above pharmaceutical composition may be supplemented with an active ingredient of another medicament for the treatment of the above mentioned diseases. The type of pharmaceutical composition is not particularly limited, and the composition may be provided as any formulation for oral or parenteral administration. For example, the pharmaceutical composition may be formulated, for example, in the form of pharmaceutical compositions for oral administration such as granules, fine granules, powders, hard capsules, soft capsules, syrups, emulsions, suspensions, solutions and the like, or in the form of pharmaceutical compositions for parenteral administrations such as injections for intravenous, intramuscular, or subcutaneous administration, drip infusions, transdermal preparations, transmucosal preparations, nasal drops, inhalants, suppositories and the like. Injections or drip infusions may be prepared as powdery preparations such as in the form of lyophilized preparations, and may be used by dissolving just before use in an appropriate aqueous medium such as physiological saline. Sustained-release preparations such as those coated with a polymer may be directly administered intracerebrally.

Types of pharmaceutical additives used for the manufacture of the pharmaceutical composition, content ratios of the pharmaceutical additives relative to the active ingredient, and methods for preparing the pharmaceutical composition may be appropriately chosen by those skilled in the art. Inorganic or organic substances, or solid or liquid substances may be used as pharmaceutical additives. Generally, the pharmaceutical additives may be incorporated in a ratio ranging from 1% by weight to 90% by weight based on the weight of an active ingredient.

Examples of excipients used for the preparation of solid pharmaceutical compositions include, for example, lactose, sucrose, starch, talc, cellulose, dextrin, kaolin, calcium carbonate and the like. For the preparation of liquid compositions for oral administration, a conventional inert diluent such as water or a vegetable oil may be used. The liquid composition may contain, in addition to the inert diluent, auxiliaries such as moistening agents, suspension aids, sweeteners, aromatics, colorants, and preservatives. The liquid composition may be filled in capsules made of an absorbable material such as gelatin. Examples of solvents or suspension mediums used for the preparation of compositions for parenteral administration, e.g. injections, suppositories, include water, propylene glycol, polyethylene glycol, benzyl alcohol, ethyl oleate, lecithin and the like. Examples of base materials used for suppositories include, for example, cacao butter, emulsified cacao butter, lauric lipid, witepsol.

The dose and frequency of administration of the medicament of the present invention are not particularly limited, and they may be appropriately chosen depending on conditions such as a purpose of preventive and/or therapeutic treatment, a type of a disease, the body weight or age of a patient, severity of a disease and the like. Generally, a daily dose for oral administration to an adult may be 0.01 to 1,000 mg (the weight of an active ingredient), and the dose may be administered once a day or several times a day as divided portions, or once in several days. When the medicament is used as an injection, administrations may preferably be performed continuously or intermittently in a daily dose of 0.001 to 100 mg (the weight of an active ingredient) to an adult.

CHEMICAL EXAMPLES

Example 1

Compound N° 1 of Table 1

Ethyl-1'-[(2S)-2-hydroxy-2-phenylethyl]-6'-oxo-8'-(pyridin-4-yl)-1',3',4',6'-tetrahydro-1H-spiro[piperidine-4,2'-pyrimido[1,2-a]pyrimidine]-1-carboxylate. (1:1) (hydrochloride)

1.1 4-Cyanomethylene-piperidine-1-carboxylic acid ethyl ester

To a suspension of 12.85 g (321.28 mmol) of sodium hydride (60% suspension in mineral oil) in 500 ml of anhydrous tetrahydrofuran at 0° C., was added 56.91 g (321.28 mmol) of diethyl-(cyanomethyl)-phosphonate over a 10-min period. The reaction mixture was stirred for 2 h at room temperature and then 44.05 g (292.07 mmol) of 4-oxo-piperidine-1-carboxylic acid ethyl ester in 230 ml of anhydrous tetrahydrofuran was added dropwise over 30 min. The resulting mixture was stirred at room temperature for 16 h.

The mixture was dissolved in 1 l of diethyl ether and washed with a saturated aqueous solution of ammonium chloride, saturated aqueous sodium chloride, dried over sodium sulfate and evaporated. The crude product was triturated with petroleum ether and filtered to afford 51.63 g of pure product as a yellow solid.

Mp: 95-96° C.

1.2 4-Amino-4-cyanomethyl-piperidine-1-carboxylic acid ethyl ester

A solution of 51.38 g (264.53 mol) of 4-cyanomethylene-piperidine-1-carboxylic acid ethyl ester in 301 ml of an aqueous ammonia solution (29%) and 50 ml of methanol was heated at 110° C. in a sealed tube for 48 h. The reaction mixture was concentrated, and the residue was chromatographed on silica gel eluting with a mixture of dichloromethane/methanol in the proportions 100/0 to 96/4 to afford 40 g of the product as a white solid.

Mp: 68-69° C.

1.3 4-tert-Butoxycarbonylamino-4-cyanomethyl-piperidine-1-carboxylic acid ethyl ester To a solution of 35.44 g (167.79 mmol) of 4-amino-4-cyanomethyl-piperidine-1-carboxylic acid ethyl ester in 200 ml of tetrahydrofuran was added 4.3 ml of water, 23.58 ml (167.79 mmol) of triethylamine and 36.61 g (167.79 mmol) of di-tert-butyl dicarbonate in 50 ml of tetrahydrofuran. The resulting mixture was stirred at room temperature for 16 h.

The mixture was dissolved in dichloromethane and washed with a saturated aqueous solution of ammonium chloride, saturated aqueous sodium chloride, dried over sodium sulfate and evaporated. The crude product was triturated with pentane and filtered to afford 46.49 g of pure product as a white solid.

Mp: 133-135° C.

1.4 4-(2-Amino-ethyl)-4-tert-butoxycarbonylamino-piperidine-1-carboxylic acid ethyl ester To a solution of 5 g (16.06 mmol) of 4-tert-butoxycarbonylamino-4-cyanomethyl-piperidine-1-carboxylic acid ethyl ester in 107 ml of methanol was added 4.71 g of Raney Nickel catalyst. The suspension was hydrogenated under 55 psi pressure at room temperature during 3 h.

The catalyst was removed by filtration and the solvent evaporated under reduced pressure. Purification by chromatography on silica gel eluting with a mixture of dichloromethane/methanol/aqueous ammonia solution (29%) in the proportions 100/0/0 to 70/30/3 led to compound in the form of an oil (2.86 g).

1.5 4-Amino-4-(2-amino-ethyl)-piperidine-1-carboxylic acid ethyl ester hydrochloride (2:1)

To a solution of 3.01 g (9.56 mmol) of 4-(2-amino-ethyl)-4-tert-butoxycarbonylamino-piperidine-1-carboxylic acid ethyl ester in 19 ml of isopropanol was added 8 ml of a solution of hydrochloric acid (5.6 N) in isopropanol and the resulting solution was stirred at room temperature for 3 h.

The mixture was cooled and diethyl ether was added. The resulting precipitate was filtered. The product was dried to give 2.49 g of pure compound as a white solid.

Mp: 119-121° C.

1.6 2-Amino-1,3,9-triaza-spiro[5.5]undec-2-ene-9-carboxylic acid ethyl ester hydrobromide (1:1)

To a solution of 15.65 g (54.33 mmol) of 4-amino-4-(2-amino-ethyl)-piperidine-1-carboxylic acid ethyl ester hydrochloride (2:1) in 108 ml of methanol was added 21.73 ml (114.09 mmol) of a solution of sodium methoxide in methanol (5.55 N). The mixture was stirred at room temperature for 2 h. The precipitate was filtered and the filtrate was evaporated. The crude was dissolved in 108 ml of water and 5.75 g (54.33 mmol) of cyanogen bromide was added portion wise. The resulting mixture was stirred at room temperature for 16 h, evaporated to dryness, dissolved in ethanol and evaporated to dryness to give 17.56 g of pure compound as a brown solid.

1.7 Ethyl 6'-oxo- 8'-(pyridin4-yl)-1',3',4',6'-tetrahydro-1H-spiro [piperidine-4,2'-pyrimido[1,2-a]pyrimidine]-1-carboxylate A mixture of 3 g (15.57 mmol) of ethyl 3-(pyridin-4-yl)-3-oxopropionate, 5 g (15.57 mmol) of 2-amino-1,3,9-triaza-spiro[5.5]undec-2-ene-9-carboxylic acid ethyl ester hydrobromide (1:1) and 4.52 g (32.70 mmol) of potassium carbonate in 28 ml of ethanol was heated at reflux temperature during 12 h.

The cooled solution was evaporated to removed solvent. The mixture was dissolved in dichloromethane and washed with a saturated aqueous solution of ammonium chloride, dried over sodium sulfate and evaporated. The residue was treated with water and the precipitate was filtered, the crude product was triturated with diethyl ether and filtered to afford 2.94 g of pure product as a white solid.

Mp: 209-210° C.

1.8 Ethyl-1'-[(2S)-2-hydroxy-2-phenylethyl]-6'-oxo-8'-(pyridin-4-yl) -1',3',4',6'-tetrahydro-1H-spiro[piperidine-4,2'-pyrimido[1,2-a]pyrimidine]-1-carboxylate. (1:1) (hydrochloride)

To a solution of 0.6 g (1.62 mmol) of ethyl 6'-oxo-8'-(pyridin-4-yl)-1',3',4',6'-tetrahydro-1H-spiro[piperidine-4, 2'-pyrimido[1,2-a]pyrimidine]-1-carboxylate in 13 ml of anhydrous dimethylformamide was added 0.085 g (2.11 mmol) of sodium hydride (60% suspension in mineral oil). The mixture was allowed to stir at 50° C. for 1 h. Then 0.25 g (2.11 mmol) of (S)-phenyloxirane was added and the mixture allowed to stir at 110° C. for 12 h.

0.25 g (2.11 mmol) of (S)-phenyloxirane was added and the mixture allowed to stir at 110° C. for 6 h. Water was added and the mixture extracted with dichloromethane. The extracts were washed with a saturated aqueous solution of sodium chloride, dried and evaporated to give crude product. Purification by chromatography on silica gel eluting with a mixture of ethyl dichloromethane/methanol in the proportions 100/0 to 90/10 led to compound in the form of free base. The base was transformed into its hydrochloride salt to give 0.144 g of pure product.

Mp: 169-170° C., $[\alpha]_D=-13.7°$ (c=0.99, dimethylsulfoxide).

$^1$H NMR (DMSO-d$^6$; 200 MHz)

δ (ppm): 8.95 (br d, 2H); 8.35 (d, 2H); 7.12-7.42 (m, 5H); 6.66 (s, 1H); 5.02 (m, 1H); 4.00 (q, 2H); 3.52-3.95 (m, 6H); 2.78-3.11 (m, 2H); 1.95-2.4 (m, 4H); 1.65-1.90 (m, 2H); 71.15 (t, 3H).

Example 2 (Compound N° 2 of Table 1)

Ethyl-6'-oxo-1'-[2-oxo-2-phenylethyl]-8'-(pyridin-4-yl)-1',3',4',6'-tetrahydro-1H -spiro [piperidine-4,2'-pyrimido[1,2-a]pyrimidine]-1-carboxylate. (1:1) (hydrochloride)

0.138 g (0.28 mmol) of ethyl-1'-[(2S)-2-hydroxy-2-phenylethyl]-6'-oxo-8'-(pyridin-4-yl) -1',3',4',6'-tetrahydro-1H-spiro[piperidine-4,2'-pyrimido[1,2-a]pyrimidine]-1-carboxylate was dissolved in 2.82 ml of anhydrous dichloromethane and mixed with 0.049 g (0.42 mmol) of N-methylmorpholine N-oxide, 0.001 g (0.0083 mmol) of tetra-n-propylammonium perruthenate and 1 g of powdered molecular sieves (4A). The mixture was stirred at 20° C. under nitrogen atmosphere for 12 h.

0.049 g (0.42 mmol) of N-methylmorpholine N-oxide, 0.001 g (0.0014 mmol) of tetra-n-propylammonium perruthenate and 1 g of powdered molecular sieves (4A) were added and the mixture was stirred at 20° C. under nitrogen atmosphere for 3 h.

Purification of the crude by chromatography on silica gel eluting with a mixture of dichloromethane/methanol in the proportions 100/0 to 95/5 gave the compound in the form of free base which was transformed into its hydrochloride salt to give 0.045 g of pure product.

Mp: 227-229° C.

$^1$H NMR (DMSO-d$^6$; 200 MHz)

δ (ppm): 8.46 (br d, 2H); 8.05 (d, 2H); 7.51-782 (m, 5H); 6.63 (s, 1H); 5.22 (s, 2H); 3.85-4.08 (m, 6H); 2.89-3.25 (m, 2H); 2.21-2.37 (m, 2H); 1.95 (td, 2H); 1.66 (d, 2H); 1.15 (t, 3H).

Example 3

Compound N° 3 of Table 1

1'-[(2S)-2-Hydroxy-2-phenylethyl]-1-methyl-8'-(pyridin-4-yl)-3',4'-dihydrospiro[piperidine-4,2'-pyrimido[1,2-a]pyrimidin]-6'(1'H)-one. (2:1) (Hydrochloride)

3.1 1-Methyl-8'-(pyridin-4-yl)-3',4'-dihydrospiro [piperidine-4,2'-pyrimido [1,2-a]pyrimidin]-6'(1'H)-one To a solution of 0.6 g (1.62 mmol) of ethyl 6'-oxo-8'-(pyridin-4-yl)-1',3',4',6'-tetrahydro-1H-spiro[piperidine4,2'-pyrimido[1,2-a]pyrimidine]-1-carboxylate dissolved in 3.25 ml of tetrahydrofuran at 0° C. was added 0.185 g (4.87 mmol) of lithium aluminium hydride. The resulting mixture was stirred at room temperature under nitrogen atmosphere for 3 h.

The reaction mixture was treated with excess of a saturated aqueous solution of sodium sulfate. Further solid sodium sulfate was added and the organic phase was filtered to remove salts. The solvent was evaporated and purification by chromatography on silica gel eluting with a mixture of dichloromethane/methanol in the proportions 100/0 to 70/30 led to compound in the form of a yellow solid (0.328 g).

Mp: 232-234° C.

3.2 1'-[(2S)-2-Hydroxy-2-phenylethyl]-1-methyl-8'-(pyridin-4-yl)-3',4'-dihydrospiro [piperidine-4,2'-pyrimido[1,2-a]pyrimidin]-6'(1'H)-one. (2:1) (hydrochloride)

The product was obtained by analogy with the method described in step 1.9 and using 1-methyl-8'-(pyridin-4-yl)-3', 4'-dihydrospiro[piperidine-4,2'-pyrimido[1,2-a]pyrimidin]-6'(1'H)-one.

Mp: 271-272° C., [α]$_D$=−10.2° (c=0.829, CH$_3$OH).

$^1$H NMR (DMSO-d$^6$; 200 MHz)

δ (ppm): 10.75 (br s, 1H); 8.91 (d, 2H); 8.31 (d, 2H); 7.20-759 (m, 5H); 6.71 (s, 1H); 5.12 (m, 1H); 3.58-4.50 (m, 4H) ; 3.00-3.45 (m, 4H); 2.85 (m, 1H); 2.75 (s, 3H) 2.08-2.44 (m, 3H) ; 1.89 (br d, 1H); 1.45 (br d, 1H).

Example 4

Compound N° 5 of Table 1

Ethyl-1'-[(2S)-2-hydroxy-2-phenylethyl]-6'-oxo-8'-(pyrimidin-4-yl)-1',3',4',6'-tetrahydro-1H-spiro[piperidine-4,2'-pyrimido[1,2-a]pyrimidine]-1-carboxylate 4.1 Ethyl 6'-oxo-8'-(pyrimidinyl-4-yl)-1',3',4',6'-tetrahydro-1H-spiro [piperidine-4,2'-pyrimido[1,2-a] pyrimidine]-1-carboxylate The product was obtained by analogy with the method described in example 1 (step 1.7) and using 3-oxo-3-pyrimidin-4-yl-propionic acid methyl ester.

Mp: 231-233° C.

4.2 Ethyl-1'-[(2S)-2-hydroxy-2-phenylethyl]-6'-oxo-8'-(pyrimidin-4-yl)-1',3',4',6'-tetrahydro-1H-spiro [piperidine-4,2'-pyrimido[1,2-a]pyrimidine]-1-carboxylate The product was obtained by analogy with the method described in step 1.8 and using ethyl 6'-oxo-8'-(pyrimidinyl-4-yl)-1',3',4',6'-tetrahydro-1H-spiro[piperidine-4,2'-pyrimido [1,2-a]pyrimidine]-1-carboxylate.

Mp: 118-120° C., [α]$_D$=−13.2° (c=1.028, CH$_3$OH).

$^1$NMH (DMSO-d$^6$; 200 MHz) δ (ppm): 9.27 (s, 1H); 8.98 (d, 1H) ; 8.10 (d, 1H); 7.15-7.43 (m, 5H); 6.70 (s, 1H); 5.48 (d, 1H); 5.05 (m, 1H); 4.04 (q, 2H); 3.52-4.10 (m, 5H); 2.92 (br q, 2H); 1.90-2.39 (m, 3H); 1.63-1.90 (m, 3H); 1.15 (t, 3H).

Example 5

Compound N° 7 of Table 1

1'-[(2S)-2-Hydroxy-2-phenylethyl]-1-methyl-8'-(pyrimidin-4-yl)-3',4'-dihydrospiro [piperidine-4,2'-pyrimido[1,2-a]pyrimidin]-6'(1'H)-one 5.1 1-Methyl-8'-(pyrimidin-4-yl)-3',4'-dihydrospiro [piperidine-4,2'-pyrimido [1,2-a]pyrimidin]-6'(1'H)-one The product was obtained by analogy with the method described in example 3 (step 3.1) and using 3-oxo-3-pyrimidin-4-yl-propionic acid methyl ester.

Mp: 194-196° C.

5.2 1'-[(2S)-2-Hydroxy-2-phenylethyl]-1-methyl-8'-(pyrimidin-4-yl)-3',4'-dihydrospiro [piperidine4,2'-pyrimido[1,2-a]pyrimidin]-6'(1'H)-one The product was obtained by analogy with the method described in step 1.8 and using 1-methyl-8'-(pyrimidin-4-yl)-3',4'-dihydrospiro[piperidine-4,2'-pyrimido [1,2-a]pyrimidin]-6'(1'H)-one.

Mp: 180-182° C.

$^1$NMH (DMSO-d$^6$; 200 MHz) δ (ppm): 9.35 (s, 1H); 9.05 (d, 1H);8.17 (d, 1H); 7.25-7.45 (m, 5H); 6.75 (s, 1H); 5.57 (d, 1H); 5.10 (m, 1H); 3.67-4.05 (m, 4H); 2.67 (br dd, 2H); 2.22 (s, 3H); 1.82-2.35 (m, 5H); 1.67 (br d, 1H); 1.20 (m, 1H).

Example 6

Compound N° 7 of table 1

Ethyl 1-[(2S)-2-hydroxy-2-phenylethyl]6-oxo-8-pyridin-4-yl-1,3,4,6-tetrahydro-1'H-spiro[pyrimido [1,2-a]pyrimidine-2,3'-pyrrolidine]-1'-carboxylate (1:1) (hydrochloride)

6.1 3-Cyanomethylene-pyrrolidine-1-carboxylic acid ethyl ester

The product was obtained by analogy with the method described in example 1.1 (step1.1)and using 3-oxo-pyrrolidine-1-carboxylic acid ethyl ester prepared according to Visconti, M et al. *Helvetica Chimica Acta* 1967, 50 (5) 1289-93.

6.2 Ethyl 3-amino-3-(cyanomethyl)pyrrolidine-1-carboxylate

The product was obtained by analogy with the method described in example 1.1 (step1.1) and using 3-cyanomethylene-pyrrolidine-1-carboxylic acid ethyl ester.

6.3 Ethyl 3-](tert-butoxycarbonyl)amino]-3-(cyanomethyl)pyrrolidine-1-carboxylate The product was obtained by analogy with the method described in example 1(step1.3) and using ethyl 3-amino-3-(cyanomethyl)pyrrolidine-1-carboxylate.

6.4 Ethyl 3-(2-aminoethyl)-3-[(tert-butoxycarbonyl) amino]pyrrolidine-1-carboxylate The product was obtained by analogy with the method described in example 1(step1.4) and using ethyl 3-[(tert-butoxycarbonyl)amino]-3-(cyanomethyl) pyrrolidine-1-carboxylate.

6.5 Ethyl 3-amino-3-(2-aminoethyl)pyrrolidine-1-carboxylate hydrochloride (2:1)

The product was obtained by analogy with the method described in example 1,(step1.5) and using ethyl 3-(2-aminoethyl)-3-[(tert-butoxycarbonyl)amino]pyrrolidine-1-carboxylate.

6.6 Ethyl 7-amino-2,6,8-triazaspiro[4.5]dec-6-ene-2-carboxylate hydrobromide (1:1)

The product was obtained by analogy with the method described in example 1(step1.6) and using ethyl 3-amino-3-(2-aminoethyl)pyrrolidine-1-carboxylate hydrochloride (2:1)

6.7Ethyl 6-oxo-8-pyridin-4-yl-1,3,4,6-tetrahydro-1'H-spiro[pyrimido[1,2-a]pyrimidine-2,3'-pyrrolidine]-1'carboxylate The product was obtained by analog with the method described in example 1(step 1.7) and using 3-oxo-3-pyridin-4-yl-propionic acid ethyl ester and ethyl 7-amino-2,6,8-triazaspiro[4.5]dec-6-ene-2-carboxylate hydrobromide (1:1).

Mp: 171-172° C.

6.8Ethyl1-[(2S)-2-hydroxy-2-phenylethyl]6-oxo-8-(pyridin-4-yl)-1,3,4,6-tetrahydro-1'H-spiro[pyrimido [1,2-a]pyrimidine-2,3'-pyrrolidine]-1'-carboxylate(1: 1) (hydrochloride)

The product was obtained by analog with the method described in example 1(step 1.8) and using ethyl 6-oxo-8-pyridin-4-yl-1,3,4,6-tetrahydro-1'H-spiro[pyrimido[1,2-a] pyrimidine-2,3'-pyrrolidine]-1'carboxylate Mp: 194-195° C. $^1$H NMR (DMSO-d$^6$; 200 MHz); δ(ppm): 8.87 (m, 2H); 8.26 (m, 2H); 7.14-7.46 (m, 5H); 6.65 (br s, 1H); 5.19 (br s, 1H); 2.88-4.36 (m, 10H); 1.71-2.28 (m, 4H); 1.13(t, 3H).

Example 7

Compound N° 2 of table 2

Ethyl 6-oxo-1(2-oxo-2phenylethyl)-8-(pyridin-4-yl)-1,3,4,6-tetrahydro-1'H-spiro[pyrimido[1,2-a]pyrimidine-2,3'-pyrrolidine]-1'carboxylate (1:1) (hydrochloride)

The product was obtained by analogy with the method described in example 2 and using ethyl 1-[(2S)-2-hydroxy-2-phenylethyl]6-oxo-8-(pyridin-4-yl)-1,3,4,6-tetrahydro-1'H-spiro[pyrimido[1,2-a]pyrimidine-2,3'-pyrrolidine]-1'-carboxylate. Mp: 190-191° C. $^1$H NMR (DMSO-d$^6$; 200 MHz); δ(ppm): 8.51 (d, 2H); 8.05 (d, 2H); 7.79 (d, 2H); 7.69 (d, 1H); 7.57 (t, 2H); 6.59 (s, 1H); 5.25 (dd, 2H); 3.82-4.18(m, 2H); 3.98 (q, 2H); 3.22-3.56(m, 4H); 1.85-2.46(m, 4H); 1.12(t, 3H).

Example 8

Compound N° 7 of table 2

1'-(3-Fluorobenzoyl)-1-[(2S)-2-hydroxy-2-phenylethyl]-8-pyrimidin-4-yl-3,4-dihydrospiro [pyrimido [1,2-a]pyrimidine-2,3'-pyrrolidin]-6(1H)-one 8.1 8-Pyrimidin-4-yl-3,4-dihydrospiro [pyrimido[1, 2-a]pyrimidine-2,3'-pyrrolidin]-6(1H)-one 1.0 g (2.81 mmol) of ethyl 6-oxo-8-pyrimidin-4-yl-1,3,4, 6-tetrahydro-1'H-spiro [pyrimido[1,2-a]pyrimidine-2,3'-pyrrolidine]-1'-carboxylate was dissolved in 25ml of a solution of hydrobromic acid (33% in acetic acid) and the resulting solution was stirred at 100° C. for 12h.

The mixture was cooled and diethyl ether was added. The resulting precipitate was filtered. The product was dissolved in a concentrated aqueous sodium hydroxide solution (30%) and the resulting solution extracted with a mixture of dichloromethane/methanol/concentrated aqueous ammonia solution in the proportions of 100/0/0 to 70/30/3. The extracts were dried with sodium sulfate and evaporated to give crude product. The crude product was triturated in diethyl ether to give 0.64 g (86%) of yellow solid. Mp: 226-228° C.

8.2 1'-(3-Fluorobenzoyl)-8-pyrimidin-4-yl-3,4-dihydrospiro[pyrimido[1,2-a]pyrimidine-2,3'-pyrrolidin]-6(1H)-one To a solution of 0.3 g (1.055 mmol) of 8-pyrimidin-4-yl-3,4-dihydrospiro [pyrimido[1,2-a]pyrimidine-2,3'-pyrrolidin]-6(1H)-one dissolved in 5 ml of tetrahydrofuran at room temperature were added 0.18 ml (1.27 mmol) of triethylamine and 0.152 ml (1.27 mmol) of 3-fluoro-benzoyl chloride. The resulting mixture was stirred at room temperature under nitrogen atmosphere for 2h. The reaction mixture was added to a saturated aqueous solution of ammonium chloride, extracted with a mixture of dichloromethane/menthanol in the proportions of 100/0 to 80/20, dried and evaporated. The residue was purified by chromatography on silica gel eluting with a mixture of dichloromethane/menthanol in the proportions of 100/0 to 70/30 to give 0.310 g (72%) of pure product as grey solid. Mp: 296-298° C.

8.3 1'-(3-Fluorobenzoyl)-1-[(2S)-2-hydroxy-2-phenylethyl]-8-pyrimidin-4-yl-3,4-dihydrospiro [pyrimido[1,2-a]pyrimidine-2,3'-pyrrolidin]-6(1H)-one The product was obtained by analogy with the method described in example 1 (step 1.8) and using 1'-(3-fluorobenzoyl)-8-pyrimidin-4-yl-3,4-dihydrospiro [pyrimido[1,2-a]pyrimidine-2,3'-pyrrolidin]-6(1H)-one Mp: 180-182° C.

$^1$H NMR (DMSO-d$^6$; 200 MHz); δ(ppm): 9.28 (s, 1H); 9.01 (t, 1H); 8.11-8.21 (m, 1H); 7.02-7.63 (m, 9H); 6.72 (s, 1H); 5.53 (AB, 1H); 5.04-5.31 (m, 1H); 3.12-4.11 (m, 8H); 1.65-2.33 (m, 4H).

Example 9

Compound N° 8 of table 2

1'-(3-Fluorobenzoyl)-1-(2-oxo-2-phenylethyl)-8-pyrimidin-4-yl-3,4-dihydrospiro [pyrimido[1,2-a] pyrimidine-2,3'-pyrrolidin]-6(1H)-one The product was obtained by analogy with the method described in example 2 and using 1'-(3-fluorobenzoyl)-1-[(2S)-2-hydroxy-2-phenylethyl]-8-pyrimidin-4-yl-3,4-dihydrospiro [pyrimido[1,2-a]pyrimidine-2,3'-pyrrolidin]-6 (1H)-one. Mp: 267-268° C. $^1$H NMR (DMSO-d$^6$; 200 MHz); δ(ppm): 9.15 (s, 1H); 8.42 (d, 1H); 8.09(t, 2H); 7.74 (t, 1H); 7.61 (t, 2H); 7.20-7.53 (m, 5H); 6.60-6.75 (m, 1H); 5.13-5.40 (m, 2H); 3.87-4.25(m, 2H); 3.37-3.87 (m, 4H); 1.84-2.52 (m, 4H).

A list of chemical structures and physical data for compounds of the aforementioned formula (I), illustrating the present invention, is given in tables 1. and 2. The compounds have been prepared according to the methods of the examples.

In the tables, Ph represents a phenyl group, Et represents an ethyl group; (S), (R) or (Rac.) in the column "Y" indicates the stereochemistry of the carbon atom:

(rac.) means racemic mixture (R) means absolute R configuration (S) means absolute S configuration In table 1, R1 is an unsubstituted pyrimidin-4-yl group or an unsubstituted pyridin-4-yl group, p, o and m represent 2, q represents 0.

TABLE 1

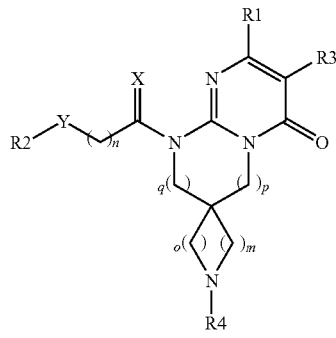

| N° | R2 | Y | X | R1 | R4 | R3 | n | Mp ° C. | salt |
|---|---|---|---|---|---|---|---|---|---|
| 1 | Ph | CH(OH)(S) | H, H | pyridin-4-yl | CO₂Et | H | 0 | 169-170 | (1:1) (hydrochloride) |
| 2 | Ph | CO | H, H | pyridin-4-yl | CO₂Et | H | 0 | 227-229 | (1:1) (hydrochloride) |

TABLE 1-continued
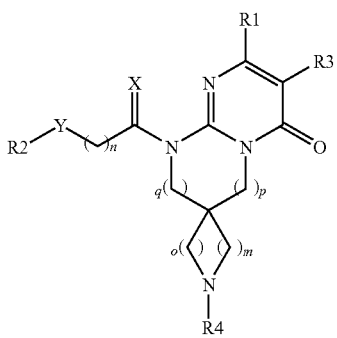
| N° | R2 | Y | X | R1 | R4 | R3 | n | Mp ° C. | salt |
|---|---|---|---|---|---|---|---|---|---|
| 3 | Ph | CH(OH)(S) | H, H | 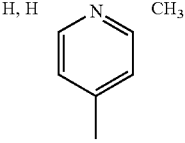 | CH₃ | H | 0 | 271-272 | (2:1) (hydrochloride) |
| 4 | Ph | CO | H, H | 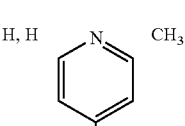 | CH₃ | H | 0 | 306-307 | (2:1) (hydrochloride) |
| 5 | Ph | CH(OH)(S) | H, H | 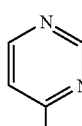 | CO₂Et | H | 0 | 118-120 | Free base |
| 6 | Ph | CO | H, H | 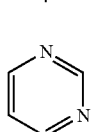 | CO₂Et | H | 0 | 179-181 | Free base |
| 7 | Ph | CH(OH)(S) | H, H | 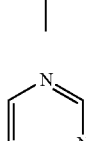 | CH₃ | H | 0 | 180-182 | Free base |
| 8 | Ph | CH(OH)(S) | H, H | 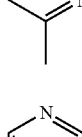 | 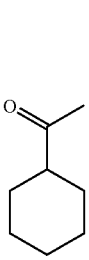 | H | 0 | 155-157 | Free base |
| 9 | Ph | CO | H, H | 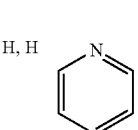 | 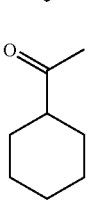 | H | 0 | 273-275 | Free base |

TABLE 1-continued
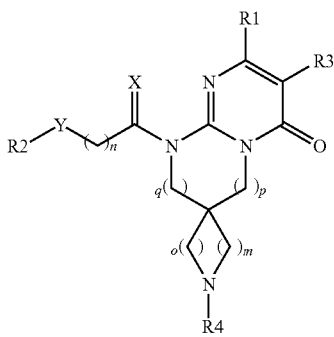
| N° | R2 | Y | X | R1 | R4 | R3 | n | Mp ° C. | salt |
|----|----|----|------|------|------|----|---|---------|------|
| 10 | Ph | CH(OH)(S) | H, H | 4-pyridyl | 3-F-benzoyl | H | 0 | 178-180 | Free base |
| 11 | Ph | CO | H, H | 4-pyridyl | 3-F-benzoyl | H | 0 | 273-275 | Free base |
| 12 | Ph | CH(OH)(S) | H, H | 4-pyridyl | cyclobutyl-C(O) | H | 0 | 149-151 | Free base |
| 13 | Ph | CO | H, H | 4-pyridyl | cyclobutyl-C(O) | H | 0 | 170-172 | Free base |
| 14 | Ph | CH(OH)(S) | H, H | 4-pyridyl | cyclopropyl-C(O) | H | 0 | 153-155 | Free base |
| 15 | Ph | CO | H, H | 4-pyridyl | cyclopropyl-C(O) | H | 0 | Lundi 15/11 | Free base |
| 16 | Ph | CO | H, H | 4-pyrimidinyl | CH₃ | H | 0 | 177-179 | Free base |

In table 2, R1 is an unsubstituted pyridin-4-yl group, or, an unsubstituted pyrimidin-4-yl group, p, m represent 2, o represents 1 and q represents 0.

TABLE 2

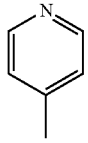

(I)

| N° | R2 | Y | X | R1 | R4 | R3 | n | Mp ° C. | salt |
|----|----|----|----|----|----|----|---|---------|------|
| 1 | Ph | CH(OH)(S) | H, H | 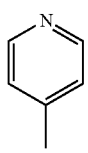 pyridin-4-yl | $CO_2Et$ | H | 0 | 194-195 | (1:1) (hydrochloride) |
| 2 | Ph | CO | H, H | pyridin-4-yl | $CO_2Et$ | H | 0 | 190-191 | (1:1) (hydrochloride) |
| 3 | Ph | CH(OH)(S) | H, H | pyridin-4-yl | $CH_3$ | H | 0 | 253-254 | (2:1) (hydrochloride) |
| 4 | Ph | CO | H, H | pyridin-4-yl | $CH_3$ | H | 0 | 231-232 | (2:1) (hydrochloride) |
| 5 | Ph | CH(OH)(S) | H, H | pyrimidin-4-yl | $CO_2Et$ | H | 0 | 149-151 | Free base |
| 6 | Ph | CO | H, H | pyrimidin-4-yl | $CO_2Et$ | H | 0 | 136-137 | Free base |
| 7 | Ph | CH(OH)(S) | H, H | pyrimidin-4-yl | 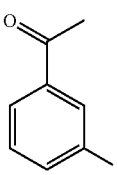 3-fluorobenzoyl | H | 0 | 180-182 | Free base |

TABLE 2-continued
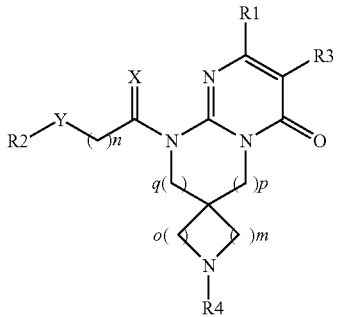
(I)
| N° | R2 | Y | X | R1 | R4 | R3 | n | Mp ° C. | salt |
|---|---|---|---|---|---|---|---|---|---|
| 8 | Ph | CO | H, H | 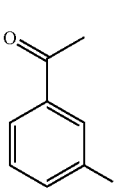 pyrimidine | 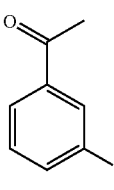 3-F-benzoyl | H | 0 | 267-268 | Free base |
| 9 | Ph | CH(OH)(S) | H, H | pyridine | 3-F-benzoyl | H | 0 | 236-238 | Free base |
| 10 | Ph | CO | H, H | pyridine | 3-F-benzoyl | H | 0 | 289-291 | Free base |
| 11 | Ph | CH(OH)(S) | H, H | pyridine | 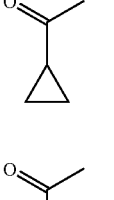 cyclopropyl-CO | H | 0 | 188-190 | Free base |
| 12 | Ph | CO | H, H | pyridine | cyclopropyl-CO | H | 0 | 282-283 | Free base |
| 13 | Ph | CH(OH)(S) | H, H | pyrimidine | cyclopropyl-CO | H | 0 | 209-210 | Free base |
| 14 | Ph | CO | H, H | pyrimidine | cyclopropyl-CO | H | 0 | 248-250 | Free base |

TABLE 2-continued
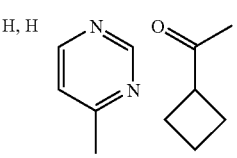
(I)
| N° | R2 | Y | X | R1 | R4 | R3 | n | Mp ° C. | salt |
|---|---|---|---|---|---|---|---|---|---|
| 15 | Ph | CH(OH)(S) | H, H | 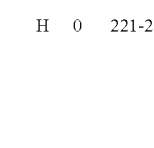 | 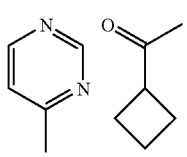 | H | 0 | 221-223 | Free base |
| 16 | Ph | CO | H, H | 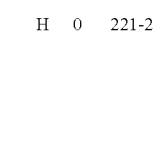 | 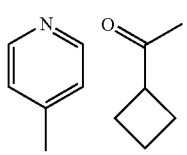 | H | 0 | 221-223 | Free base |
| 17 | Ph | CH(OH)(S) | H, H | 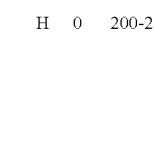 | 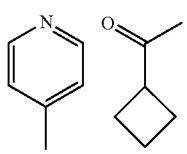 | H | 0 | 200-202 | Free base |
| 18 | Ph | CO | H, H | 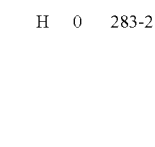 | 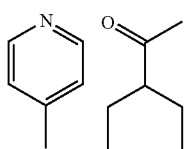 | H | 0 | 283-284 | Free base |
| 19 | Ph | CH(OH)(S) | H, H | 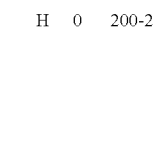 | 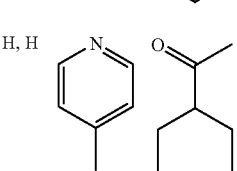 | H | 0 | 200-202 | Free base |
| 20 | Ph | CO | H, H | 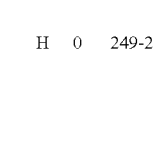 | 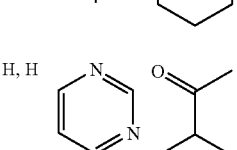 | H | 0 | 249-250 | Free base |
| 21 | Ph | CH(OH)(S) | H, H | 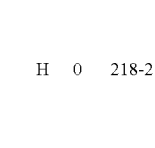 | | H | 0 | 218-219 | Free base |

TABLE 2-continued (Structure I: tricyclic pyrimidinone with spiro-azetidine, substituents R1, R2, R3, R4, X, Y, n, o, p, q, m)

| N° | R2 | Y | X | R1 | R4 | R3 | n | Mp ° C. | salt |
|----|----|----|----|----|----|----|----|----|----|
| 22 | Ph | CO | H, H | 4-methylpyrimidin-2-yl | 1-(cyclohexyl)carbonyl | H | 0 | 233-234 | Free base |

Test Example

Inhibitory activity of the medicament of the present invention against GSK3β:

Two different protocols can be used.

In a first protocol: 7.5 µM of prephosphorylated GS1 peptide and 10 µM ATP (containing 300,000 cpm of 33P-ATP) were incubated in 25 mM Tris-HCl, pH 7.5, 0.6 mM DTT 6 mM MgCl$_2$, 0.6 mM EGTA, 0.05 mg/ml BSA buffer for 1 hour at room temperature in the presence of GSK3beta (total reaction volume: 100 microliters).

In a second protocol: 4.1 µM of prephosphorylated GSI peptide and 42 µM ATP (containing 260,000 cpm 33P-ATP) were incubated in 80 mM Mes-NaOH, pH 6.5, 1 mM Mg acetate, 0.5 mM EGTA, 5 mM 2-mercaptoethanol, 0.02% Tween 20,10% glycerol buffer for 2 hours at room temperature in the presence of GSK3beta. Inhibitors were solubilised in DMSO (final solvent concentration in the reaction medium, 1%).

The reaction was stopped with 100 microliters of a solution made of 25 g polyphosphoric acid (85% P$_2$O$_5$), 126 ml 85% H$_3$PO$_4$, H$_2$O to 500 ml and then diluted to 1:100 before use. An aliquot of the reaction mixture was then transferred to Whatman P81 cation exchange filters and rinsed with the solution described above. Incorporated 33P radioactivity was determined by liquid scintillation spectrometry.

The phosphorylated GS-1 peptide had the following sequence: NH2-YRRAAVPPSPSLSRHSSPHQS(P)EDEE-COOH. (Woodgett, J. R. (1989) Analytical Biochemistry 180, 237-241, which is incorporated herein by reference in its entirety.

The GSK3β inhibitory activity of the compounds of the present invention are expressed in IC$_{50}$, and as an illustration the range of IC$_{50}$'s of the compounds in table 1 and table 2 is between 1 nanomolar to 1 micromolar concentrations.

For example compound No. 4 of table 1 shows an IC$_{50}$ of 0.007 µM and compound No. 4 of table 2 shows an IC$_{50}$ of 0.006 µM.

Formulation Example (1) Tablets

The ingredients below were mixed by an ordinary method and compressed by using a conventional apparatus.

| | |
|---|---|
| Compound of Example 1 | 30 mg |
| Crystalline cellulose | 60 mg |
| Corn starch | 100 mg |
| Lactose | 200 mg |
| Magnesium stearate | 4 mg |

(2) Soft Capsules

The ingredients below were mixed by an ordinary method and filled in soft capsules.

| | |
|---|---|
| Compound of Example 1 | 30 mg |
| Olive oil | 300 mg |
| Lecithin | 20 mg |

(1) Parenteral Preparations

The ingredients below were mixed by an ordinary method to prepare injections contained in a 1 ml ampoule.

| | |
|---|---|
| Compound of Example 1 | 3 mg |
| Sodium chloride | 4 mg |
| Distilled water for injection | 1 ml |

INDUSTRIAL APPLICABILITY

The compounds of the present invention have GSK3β inhibitory activity and are useful as an active ingredient of a medicament for preventive and/or therapeutic treatment of diseases caused by abnormal activity of GSK3β and more particularly of neurodegenerative diseases.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A method of inhibiting the activity of glycogen synthase kinase 3-beta (GSK3-β), which comprises administering to a patient in need of said inhibition a therapeutically effective amount of a compound of formula (I) or a pharmaceutically acceptable salt thereof:

wherein:
X represents two hydrogen atoms, a sulfur atom, an oxygen atom or a $C_{1-2}$ alkyl group and a hydrogen atom;
Y represents a bond, a carbonyl group, a methylene group optionally substituted by one or two groups chosen from a $C_{1-6}$ alkyl group, a hydroxyl group, a $C_{1-4}$ alkoxy group, a $C_{1-2}$ perhalogenated alkyl group or an amino group;
R1 represents a 2, 3 or 4-pyridine ring or a 2, 4 or 5-pyrimidine ring, the rings being optionally substituted by a $C_{1-4}$ alkyl group, a $C_{1-4}$ alkoxy group or a halogen atom;
R2 represents a benzene ring or a naphthalene ring; the rings being optionally substituted by 1 to 4 substituents selected from a $C_{1-6}$ alkyl group, a methylenedioxy group, a halogen atom, a $C_{1-2}$ perhalogenated alkyl group, a $C_{1-3}$ halogenated alkyl group, a hydroxyl group, a $C_{1-4}$ alkoxy group, a nitro, a cyano, an amino, a $C_{1-5}$ monoalkylamino group or a $C_{2-10}$ dialkylamino group;
R3 represents a hydrogen atom, a $C_{1-6}$ alkyl group or a halogen atom;
R4 represents a hydrogen atom, a $C_{1-4}$ alkoxy carbonyl group, a $C_{3-6}$ cycloalkyl carbonyl group, a benzoyl group, a $C_{1-6}$ alkyl group, the groups being optionally substituted by 1 to 4 substituents selected from a halogen atom, a hydroxyl group or a $C_{1-4}$ alkoxy group;
o and m represent 1 to 2;
n represents 0 to 3;
p represents 0 to 2; and
q represents 0 to 2.

2. The method according to claim 1, wherein $R_4$ represents a hydrogen atom, a $C_{1-4}$ alkoxy carbonyl group, a $C_{1-6}$ alkyl group optionally substituted by 1 to 4 substituents selected from a halogen atom, a hydroxyl group or a $C_{1-4}$ alkoxy group.

3. The method according to claim 1, wherein R1 represents an unsubstituted 4-pyridinyl group or unsubstituted 4-pyrimidinyl group.

4. The method according to claim 3, wherein
R2 represents a benzene ring, the ring being optionally substituted by 1 to 4 substituents selected from a $C_{1-3}$ alkyl group, a halogen atom, a hydroxyl group or a $C_{1-2}$ alkoxy group; and
R3 represents a hydrogen atom; and
R4 represents a $C_{1-4}$ alkoxy carbonyl group, a $C_{3-6}$ cycloalkyl carbonyl group, a benzoyl group or a $C_{1-3}$ alkyl group optionally substituted by 1 to 4 substituents selected from a halogen atom or a hydroxyl group; and
X represents two hydrogen atoms; and
Y represents a carbonyl group or a methylene group optionally substituted by a hydroxyl group; and
p represents 2 and q represents 0.

5. The method according to claim 1, wherein the compound is selected from the group consisting of:
Ethyl-1'-[(2S)-2-hydroxy-2-phenylethyl]-6'-oxo-8'-(pyridin-4-yl)-1',3 ', 4',6'tetrahydro-1H-spiro[piperidine-4, 2'-pyrimido[1,2-a]pyrimidine]-1-carboxylate
Ethyl-6'-oxo-1'-[2-oxo-2-phenylethyl]-8'-(pyridin-4-yl)-1',3',4',6'-tetrahydro-1H-spiro[piperidine-4,2'-pyrimido [1,2-a]pyrimidine]-1-carboxylate
1'-[(2S)-2-Hydroxy-2-phenylethyl]-1-methyl-8'-(.pyridin-4-yl)-3',4'-dihydrospiro [piperidine-4,2'-pyrimido[1,2-a]pyrimidin]-6'(1'H-one
1-Methyl-1'-(2-oxo-2-phenylethyl)-8'-(pyridin-4-yl)-3', 4'-dihydrospiro [piperidine-4,2'-pyrimido[1,2-a]pyrimidin]-6'(1 H)-one
Ethyl-1'-[(2S)-2-hydroxy-2-phenylethyl]-6'-oxo-8'-(pyrimidin-4-yl)-1',3',4', 6'-tetrahydro-1H-spiro[piperidine-4,2'-pyrimido[1,2-a]pyrimidine]-1-carboxylate
Ethyl-6'-oxo-1'-[2-oxo-2-phenylethyl]-8'-(pyrimidin-4-yl)-1',3',4', 6'-tetrahydro-1H-spiro [piperidine-4,2'-pyrimido[1,2-a]pyrimidine]-1-carboxylate
1-[(2S)-2-Hydroxy-2-phenylethyl]-1-methyl-8'-(pyrimidin-4-yl)-3',4',-dihydrospiro [piperidine-4,2'-pyrimido [1,2-a]pyrimidin]-6'(1'H)-one
1-(Cyclohexylcarbonyl)-1'-[(2S)-2-hydroxy-2-phenylethyl]-8'-pyridin-4-yl- 3',4'-dihyclrospiro [piperidine-4, 2'-pyrimido[1,2-a]pyrimidin]-6'(1'H)-one
1-(Cyclohexylcarbonyl)-1'-(2-oxo-2-phenylethyl)-8'-pyridin-4-yl-3',4'-dihydrospiro [piperidine-4,2'-pyrimido [1,2-a]pyrimidin]-6'(1'H)-one
1-(3-Fluorobenzoyl)-1'-[(2S)-2-hydroxy-2-phenylethy]-8'-pyridin-4-yl-3', 4'-dihydrospiro[piperidine-4,2'-pyrimido[1,2-a]pyrimidin]-6'(1'H)-one
1 (3-Fluorobeuzoyl)-1'-(2-oxo-2-phenylethyl)-8'-pyridin-4-yl-3',4'-dihydrospiro [piperidine-4,2'-pyrimido[1,2-a] pyrimidin]-6'(1'H)-one
1-(Cyclobutylcarbonyl)-1'-[(2S)-2-hydroxy-2-phenylethyl]-8'-pyridin-4-yl-3', 4'-dihydrospiro [piperidine-4, 2'-pyrimido[1,2-a]pyrimidin]-6'(1'H)-one
1-(Cyclobutylcarbonyl)-1'-(2-oxo-2-phenylethyl)-8'-pyridin-4-yl-3',4'- dihydrospiro [piperidine-4,2'-pyrimido [1,2-a]pyrimidin]-6'(1'H)-one
1-(Cyclopropylcarbonyl)-1'-[(2S)-2-hydroxy-2-phenylethyl]-8'-pyridin-4-yl-3', 4'-dihydrospiro[piperidine-4, 2'-pyrimido[1,2-a]pyrimidin]-6'(1 H)-one
1-(Cyclopropylcarbonyl)-1'-(2-oxo-2-phenylethyl)-8'-pyridin-4-yl-3',4'- dihydrospiro [piperidine-4,2'-pyrimido [1,2-a]pyrimidin]-6'(1'H)-one 1-Methyl-1-(2-oxo-2-phenylethyl)-8'-(pyrimidin-4-yl)-3',4'.dihydrospiro[piperidine-4,2'-pyrimido[1,2a]pyrimidin]'6'(1'H)-one Ethyl 1-[(2S)-2-hydroxy-2-phenylethyl]-6-oxo-8-(pyridin-4-yl)-1,3,4,6-tetrahydro-1'H-spiro [pyrimido[1,2-a]pyrimidine-2,3'-pyrrolidine]-1'-carboxylate Ethyl 6-oxo-1-(2-oxo-2-phenylethyl)-8-(pyridin-4-yl)-1,3,4,6-tetrahydro-1'H-spiro [pyrimido[1,2-a]pyrimidine-2,3'-pyrrolidine]-1'-carboxylate 1-[(2 S)-2-hydroxy-2-phenylethyl]-1'-methyl-8-(pyridin-4-yl)-3,4-dihydrospiro [pyrimido[1,2-a]pyrimidine-2,3'-pyrrolidin]-6(1 H)-one 1'-Methyl-1-(2-oxo-2-phenylethyl)-8-(pyridin-4-yl)-3,4- dihydrospiro [pyrimido[1,2-a]pyrimidine-2,3'-pyrrolidin]-6(1H)-one Ethyl 1-[(2S)-2-hydroxy-2-phenylethyl]-6-oxo-8-pyrimidin-4-yl-1,3,4,6 -tetrahydro-1'H-spiro [pyrimido[1,2-a]pyrimidine-2,3'-pyrrolidine]-1'-carboxylate Ethyl 6-oxo-1-(2-oxo-2-phenylethyl)-8-pyrimidin-4-yl-1,3,4,6-tetrahydro-1'H-spiro [pyrimido [1,2-a]pyrimidine-2,3'-pyrrolidine]-1'-carboxylate 1'-(3-Fluorobenzoyl)-1-[(2S)-2-hydroxy-2-phenylethyl]-8-pyrimidin-4-yl-3,4-dihydrospiro [pyrimido[1,2-a]pyrimidine-2,3'-pyrrolidin]-6(1 H)-one 1'-(3-Fluorobenzoyl)-1-(2-oxo-2-phenylethyl)-8-pyrimidin-4-yl-3,4-dihydrospiro [pyrimido[1,2-a]pyrimidine-2,3'-pyrrolidin]-6(1 H)-one 1'-(3-Fluorobenzoyl)-1-[(2S)-2-hydroxy-2-phenylethyl]-8-pyridin-4-yl-3,4-dihydrospiro [pyrimido[1,2-a]pyrimidine-2,3'-pyrrolidin]-6(1 H)-one 1'-(3-Fluorobenzoyl)-1-(2-oxo-2-phenylethyl)-8-pyridin-4-yl-3,4-dihydrospiro [pyrimido[1,2-a]pyrimidine-2,3'-pyrrolidin]-6(1H)-one 1'-(Cyclopropylcarbonyl)-1-[(2S)-2-hydroxy-2-phenylethyl]-8-pyridin-4-yl-3,4-dihydrospiro [pyrimido[1,2-a]pyrimidine-2,3'-pyrrolidin]-6(1 H)-one 1'-(Cyclopropylcarbonyl)-1-(2-oxo-2-phenylethyl)-8-pyridin-4-yl-3,4-dihydrospiro [pyrimido[1,2-a]pyrimidine-2,3'-pyrrolidin]-6(1H)-one 1'-(Cyclopropylcarbonyl)-1-[(2 S)-2-hydroxy-2-phenylethyl]-8-pyrimidin-4-yl- 3,4-dihydrospiro [pyrimidot 1,2-a]pyrimidine-2,3'-pyrrolidinl-6(1 H)-one 1'-(Cyclopropylcarbonyl)-1-(2-oxo-2-phenylethyl)-8-pyrimidin-4-yl-3,4-dihydrospiro [pyrimido[1,2-a]pyrimidine-2,3'-pyrrolidin]-6(1 H)-one 1'-(Cyclobutylcarbonyl)-1-[(2S)-2-hydroxy-2-phenylethyl]-8-pyrimidin-4-yl-3,4-dihydrospiro[pyrimido[1,2-a]pyrimidine-2,3'-pyrrolidin]-6(1 H)-one 1'-(Cyclobutylcarbonyl)-1-(2-oxo-2-phenylethyl)-8-pyrimidin-4-yl-3,4-dihydrospiro [pyrimido[1,2-a]pyrimidine-2,3'-pyrrolidin]-6(1 H)-one 1'-(Cyclobutylcarbonyl)-1-[(2S)-2-hydroxy-2-phenylethyl]-8-pyridin-4-yl-3,4-dihydrospiro [pyrimido[1,2-a]pyrimidine-2,3'-pyrrolidin]-6(1 H)-one 1'-(Cyclobutylcarbonyl)-1-(2-oxo-2-phenylethyl)-8-pyridin-4-yl-3,4-dihydrospiro [pyrimido[1,2-a]pyrimidine-2,3'-pyrrolidin]-6(1 H)-one 1'-(Cyclohexylcarbonyl)-1-[(2 S)-2-hydroxy-2-phenylethyl]-8-pyridin-4-yl-3,4-dihydrospiro [pyrimido[1,2-a]pyrimidine-2,3'-pyrrolidin]-6(1 H)-one 1'-(Cyclohexylcarbonyl)-1-(2-oxo-2-phenethyl)-8-pyridin-4-yl-3,4-dihydrospiro [pyrimido[1,2-a]pyrimidine-2,3'-pyrrolidin]-6(1H)-one 1'-(Cyclohexylcarbonyl)-1-[(2 S)-2-hydroxy-2-phenylethyl]-8-pyrimidin-4-yl- 3,4-dihydrospiro[pyrimido[1,2-a]pyrimidine-2,3'-pyrrolidin]-6(1H)-one 1'-(Cyclohexylcarbonyl)-1-(2-oxo-2-phenethyl)-8-pyrimidin-4-yl-3,4-dihydrospiro [pyrimido[1,2-a]pyrimidine-2,3'-pyrrolidin]-6(1 H)-one;

or a pharmaceutically acceptable salt thereof.

* * * * *